United States Patent [19]
Russell

[11] Patent Number: 5,997,550
[45] Date of Patent: Dec. 7, 1999

[54] METHOD OF INCREASING AVAILABLE HAIR GRAFTS

[76] Inventor: Kathleen S. Russell, 701 Osage Rd., Pittsburgh, Pa. 15243

[21] Appl. No.: 09/114,111

[22] Filed: Jul. 13, 1998

[51] Int. Cl.⁶ ..................................................... A61B 17/50

[52] U.S. Cl. ........................... 606/133; 606/132; 606/134

[58] Field of Search ..................................... 606/133, 131, 606/132, 134, 9–17, 184, 185, 186, 187, 167; 30/32

[56] References Cited

U.S. PATENT DOCUMENTS

| | | | |
|---|---|---|---|
| 5,417,683 | 5/1995 | Shiao | 606/1 |
| 5,817,120 | 10/1998 | Rassman | 606/187 |
| 5,899,916 | 5/1999 | Casparian | 606/187 |

*Primary Examiner*—Michael Buiz
*Assistant Examiner*—Yen Ngo
*Attorney, Agent, or Firm*—David L. Volk

[57] ABSTRACT

Grafts containing intact hair follicles are transected into smaller grafts containing transected follicles. Each smaller graft is then implanted individually into incisions within a recipient area.

18 Claims, 2 Drawing Sheets

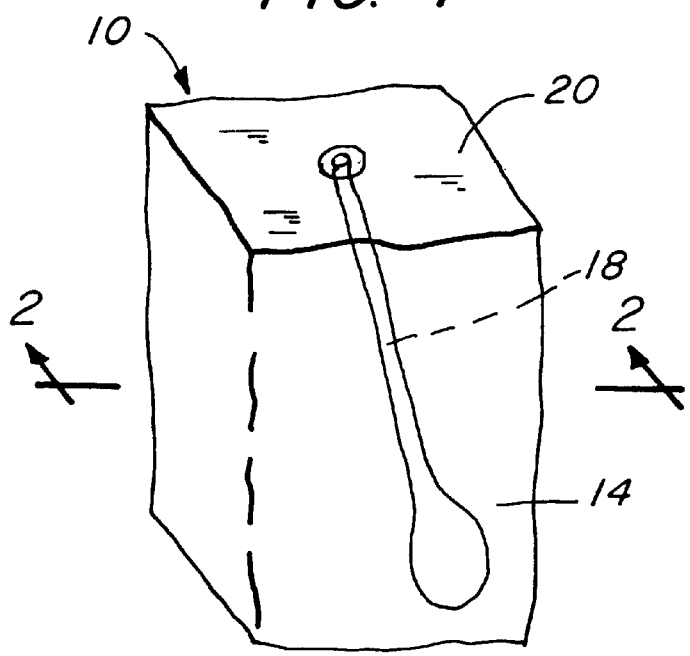
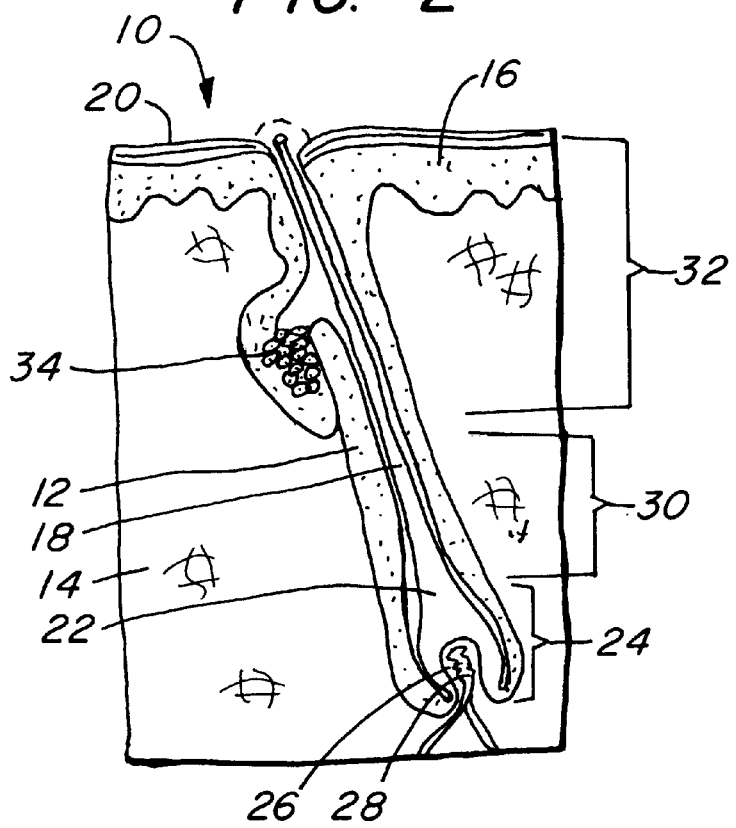

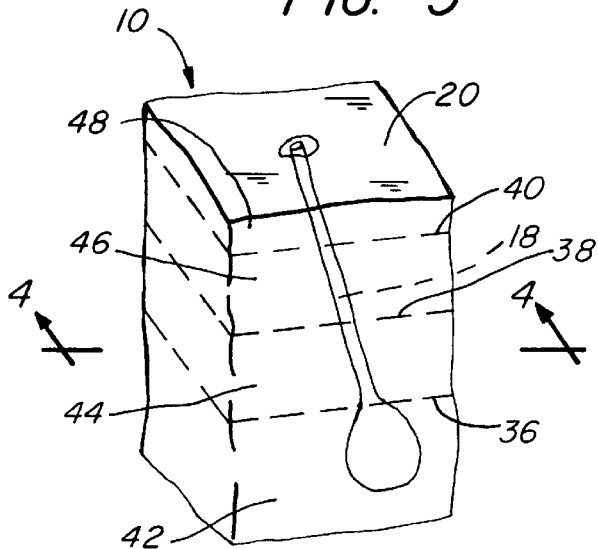
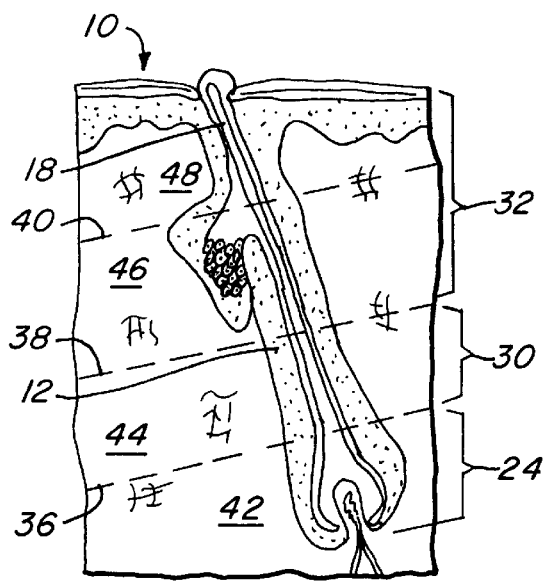
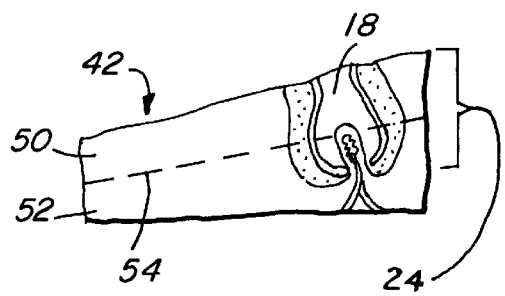

METHOD OF INCREASING AVAILABLE HAIR GRAFTS

BACKGROUND OF THE INVENTION

1. Field of the Invention

The present invention relates to hair transplantation methods.

2. Description of the Related Art

The most common method of hair transplantation today involves extracting a rectangular strip of tissue from a donor area at the back of the head. The extracted strip is deep enough to include the complete hair follicles. The strip is then cut to produce grafts, which may be split grafts (generally including 6 to 7 follicles), mini-grafts (generally including 3 to 5 follicles), or micro-grafts which include 1 or 2 follicles. The grafts are then implanted into a recipient area. Until the present invention, only grafts having entire follicles have been implanted into the recipient area.

SUMMARY OF THE INVENTION

The method of the present invention includes transecting grafts containing intact follicles into smaller grafts containing transected follicles, and implanting the smaller grafts individually into incisions within a recipient area. The inventor has found that the smaller grafts have resulted in growing hair. Thus, using the method of the present invention, a greater number of grafts can be placed into the recipient area, from a given number of follicles extracted from the donor area.

Still further features and advantages will become apparent from the ensuing description and drawings.

BRIEF DESCRIPTION OF THE DRAWINGS

FIG. 1 is a perspective view of a hair micro-graft.

FIG. 2 is a cross-sectional view of the micro-graft, taken along line 2—2 of FIG. 1.

FIG. 3 is a perspective view of the micro-graft, showing transection lines of the method of the present invention.

FIG. 4 is a cross-sectional view of the micro-graft, taken along line 4—4 of FIG. 1.

FIG. 5 is a cross-sectional view similar to FIG. 4, showing the bulb graft further transected into two portions.

DETAILED DESCRIPTION

FIG. 1 is a perspective view of a hair micro-graft 10. FIG. 2 is a cross-sectional view of the micro-graft 10, taken along line 2—2 of FIG. 1. Referring to FIGS. 1–2, the micro-graft 10 includes an entire follicle 12, and a section of tissue 14 surrounding the follicle 12. Contained within the follicle 12 is a hair 18, which has been shaved to the surface of the skin 20. The hair 18 is shaved prior to extraction of the follicles 12 from the donor area. Although the hair 18 is shown shaved to the surface of the skin 20, some doctors prefer to leave a portion of the hair 18 beyond the surface of the skin 20, to serve as a visual marker.

The tissue 14 is generally translucent; thus the hair 18 can usually be seen from outside of the micro-graft 10. The follicle 12 is a tubular down-growth of the epidermis 16. The hair 18 resides within and grows outwardly from the follicle 12. The lowest section of the hair 18 is called the root 22. The root 22 rests in a structure of the follicle called the bulb 24. The papilla 26 projects into the bulb 24 from the base of the follicle 12. The papilla 26 contains blood vessels 28 which supply the blood necessary for the growing cells of the hair 18.

As growing cells move upward from the root 22, the cells are cut off from the nourishment provided by the papilla 26, and the cells die, forming keratin, a process known as keratinization. This occurs in the keratinization zone 30. The part of the hair 18 above the keratinization zone 30 is called the shaft 32. An outgrowth of the follicle 12 contains the sebaceous gland 34, which secretes oil to the hair 18.

Until the present method, grafts transplanted into a recipient area (not shown) have always included the entire follicle 12. Conventionally, the graft is inserted into a straight incision (not shown) made in the recipient area.

FIG. 3 is a perspective view of the micro-graft 10, showing first, second, and third transection lines 36, 38, 40 of the method of the present invention. FIG. 4 is a cross-sectional view of the micro-graft 10, taken along line 4—4 of FIG. 1. FIG. 4 shows the same transection lines 36, 38, 40.

The first transection line 36 is generally just above the bulb 24, leaving a bulb graft 42 below the first transection line 36, which includes the intact bulb 24.

The second transection line 38 is generally just above a lower third of the portion of the hair 18 which is above the bulb 24. The second transection line 38 can also be described as generally at the top of the keratinization zone 30. A keratinization zone graft 44 is formed between the first and second transection lines 36, 38.

The third transection line 40 generally bisects the shaft 32, creating a lower shaft graft 46 and an upper shaft graft 48.

FIG. 5 is a cross-sectional view similar to FIG. 4, showing the bulb graft 42 further transected into an upper bulb graft 50 and a lower bulb graft 52, along a fourth transection line 54.

The transection lines 36, 38, 40, 54 are cut after the micro-grafts 10 are cut from the strip of tissue from the donor area (not shown). The transection lines 36, 38, 40, 54 are cut using a scalpel and if desired, an appropriate visual aid such as conventional loop type magnifying headgear or a microscope.

The grafts 42, 44, 46, 48, 50, 52 are then implanted into incisions (not shown) in a recipient area (not shown), in the same manner as micro-grafts and mini-grafts of the prior art are implanted.

For each type of graft 42, 44, 46, 48, 50, 52 implanted into an incision in the recipient area, the inventor has found that hair growth occurs in the recipient area at least some of the time.

It is anticipated that some of the grafts 42, 44, 46, 48, 50, 52 may be more successful than others. For example, the bulb graft 42 may consistently produce more long lasting hair growth than any of the other grafts 44, 46, 48, 50, 52.

It is also anticipated that other grafts containing transected follicles 12, taken at various locations along the follicle 12 may produce hair growth. Furthermore, some of these other grafts may prove to be more successful than the ones described herein. For example, and not by way of limitation, a graft which includes the entire shaft 32 may be more successful than the lower or upper shaft grafts 46, 48. As another example, a graft which includes generally only a lower portion of the keratinization zone 30 may prove to be successful.

Although the method has been shown and described as the transection of micro-grafts containing only one follicle, grafts having more than one follicle may be transected, creating grafts which each have more than one transected follicle.

The foregoing description is included to describe embodiments of the present invention which include the preferred embodiment, and is not meant to limit the scope of the invention. From the foregoing description, many variations will be apparent to those skilled in the art that would be encompassed by the spirit and scope of the invention. Accordingly, the scope of the invention is to be limited only by the following claims and their legal equivalents.

The invention claimed is:

1. A method of hair transplantation comprising:
   a. extracting flesh from a donor site;
   b. cutting the flesh into a plurality of grafts each comprising at least one intact follicle;
   c. transecting at least one of the grafts into a plurality of smaller grafts, each of the smaller grafts comprising at least one transected portion of one of the intact follicles; and
   d. implanting at least some of the smaller grafts individually into incisions within a recipient site.

2. The method of claim 1, wherein at least one of the transected portions comprises an intact bulb of the follicle.

3. The method of claim 1, wherein at least one of the transected portions comprises an intact bulb transected from the follicle generally just above the bulb.

4. The method of claim 1, wherein at least one of the transected portions comprises an upper bulb portion transected from a bulb of the follicle.

5. The method of claim 1, wherein at least one of the transected portions comprises a lower bulb portion transected from a bulb of the follicle.

6. The method of claim 1, wherein at least one of the transected portions is devoid of a bulb of the follicle.

7. The method of claim 1, wherein at least one of the transected portions is generally devoid of a keratinization zone of the follicle.

8. The method of claim 1, wherein at least one of the transected portions is an upper portion of the follicle transected from the follicle generally above the keratinization zone.

9. The method of claim 1, wherein at least one of the transected portions is a single portion of the follicle transected from the follicle generally at a top of a keratinization zone and generally above a bulb of the follicle.

10. A method of hair transplantation comprising inserting hair grafts into a recipient site, wherein a plurality of the grafts each contain a transected portion of a follicle.

11. The method of claim 10, wherein at least one of the transected portions comprises an intact bulb of the follicle.

12. The method of claim 10, wherein at least one of the transected portions comprises an intact bulb transected from the follicle generally just above the bulb.

13. The method of claim 10, wherein at least one of the transected portions comprises an upper bulb portion transected from a bulb of the follicle.

14. The method of claim 10, wherein at least one of the transected portions comprises a lower bulb portion transected from a bulb of the follicle.

15. The method of claim 10, wherein at least one of the transected portions is devoid of a bulb of the follicle.

16. The method of claim 10, wherein at least one of the transected portions is generally devoid of a keratinization zone of the follicle.

17. The method of claim 10, wherein at least one of the transected portions is an upper portion of the follicle transected from the follicle generally above the keratinization zone.

18. The method of claim 10, wherein at least one of the transected portions is a single portion of the follicle transected from the follicle generally at a top of a keratinization zone and generally above a bulb of the follicle.

* * * * *